United States Patent [19]

Welter

[11] Patent Number: Plant 6,120

[45] Date of Patent: Mar. 1, 1988

[54] SYNGONIUM PLANT NAMED MAGNUM

[76] Inventor: Gary Welter, 41-875 Kakaina St., Waimanalo, Hi. 96795

[21] Appl. No.: 832,780

[22] Filed: Feb. 25, 1986

[51] Int. Cl.[4] ..... A01H 5/00

[52] U.S. Cl. ..... Plt./88

[58] Field of Search ..... Plt./88

*Primary Examiner*—Robert E. Bagwill

*Attorney, Agent, or Firm*—Schwartz, Jeffery, Schwaab, Mack, Blumenthal & Evans

[57] ABSTRACT

A new and distinct variety of *Syngonium podophyllum* named Magnum having the characteristics of large leaves, large diameter stem and petioles, with the petioles carrying the leaves very erect, and having a full appearance.

2 Drawing Figures

1

The present invention comprises a new and distinct cultivar of *Syngonium podophyllum*, known by the cultivar name Magnum.

The new cultivar was discovered by me as a spontaneous mutation growing among a group of plants of the parent cultivar in the greenhouses of Kula Mana Nursery, 41-875 Kakaina Street, Waimanalo, Hi. on Jan. 3, 1981. The parent plant was *Syngonium podophyllum* White Butterfly, a well known commercial cultivar.

The new cultivar was immediately recognized for its distinctively different characteristics when compared with the other plants of the parent cultivar. In particular, the size of the leaves of Magnum are substantially greater than White Butterfly.

After separating the new cultivar from the plants of the parent cultivar, the new cultivar was grown and thereafter asexually reproduced by me at Kula Mana Nursery, Waimanalo, Hi., by taking vegetative cuttings. Horticultural examination of subsequent generations of propagation has clearly demonstrated that the combination of characteristics as herein disclosed for Magnum are firmly fixed and are retained through successive generations of asexual reproduction.

Magnum has not been observed under all possible environmental conditions. The phenotype may vary significantly with variations in environment such as temperature, light intensity, and day length. The following observations, measurements and comparisons describe plants grown in Waimanalo, Hi., under greenhouse conditions which approximate those generally used in commercial practice.

The following traits have been repeatedly observed and are determined to be basic characteristics of Magnum which, in combination, distinguish it as a new and distinct cultivar:

1. The leaf length, measured from the apex to the base of the longest lobe is relatively long, measuring up to 20 mm. and occasionally more.

2. The leaf width, measured at or slighyly beyond the juncture of the leaf with the petiole, is similarly large, measuring up to 12 mm.

3. The stems are relatively large in diameter, thereby producing an erect, vigorous growth habit.

4. The petiole diameter is approximately 5 mm. at the junction of the sheath, with the relatively thick petioles producing strong support for the large leaves.

5. Magnum produces an abundance of leaves, thereby giving the plant a full appearance.

In the accompanying photographic drawings, the color photograph appearing at the top of the sheet illustrates in perspective view a plant approximately 9 months in age of the new cultivar grown in a 6" basket. The photograph at the bottom of the sheet is a comparison of a leaf of Magnum (on the left) with a leaf of White Butterfly (on the right).

2

Magnum can be most closely compared with the parent cultivar White Butterfly. The basic differences in Magnum will be apparent from the comparative measurements of certain characteristics set forth in Chart A attached hereto. Generally speaking, the leaves of Magnum are much larger and thicker and the plant has a fuller appearance, with the leaves being carried erect on very strong stems and petioles. Leaf color is generally the same.

The following description is based on observations and measurements of Magnum grown in the greenhouses of Kula Mana Nursery, Waimanalo, Hi. Color references are made to The Royal Horticultural Society Colour Chart. Color values were taken in mid-February in Alexandria, Va. under natural light conditions.

THE PLANT

Botanical: *Syngonium podophyllum*, c.v. Magnum.

Origin: Mutation of White Butterfly.

Form: Erect, with sturdy stems and petioles carrying the large leaves without significant drooping of the leaves despite their size.

Shape: Very full and symmetrical.

Growth: Growth habit is good and comparable to White Butterfly. However, the erect stems and larger leaves of Magnum give the appearance of a fuller plant at the same stage of growth.

Stem: Stout, 8–14 mm. in diameter.

Roots: Adventitious; stout, 2.9–3.1 mm. in diameter.

Foliage:

*Quantity.*—Abundant.

*Shape.*—Sagittate and deeply lobed; tip pinnate to acuminate; edges wavy.

*Size.*—Mature leaf blades 17–20.5 cm. long, and 10.4–11.8 cm. wide at the juncture of the petiole; 10.5–12.5 cm. long from apex to junction of the petiole. Length/width ratio is 1.5–1.8. Thickness is 0.25–0.3 mm. at the thinnest part between the major veins, substantially thicker than the leaves of White Butterfly.

*Gloss.*—Slight sheen.

*Color.*—Upper surface of mature leaves 138B-C with darkening appearing at the edges. Upper surface of younger leaves closest to 139D, although color value is not precise. Lower surface of mature leaves, 139C.

*Petioles.*—4.7–5.2 mm. in diameter at the apex of the sheath.

*Veins.*—Very prominant and thick mid-vein; other veins are typical, protruding slightly on under surface, and slightly recessed on upper surface.

Disease resistance: No susceptability to disease has been noted to date.

| | Chart A | |
|---|---|---|
| | White Butterfly | Magnum |
| Adventitious Roots (diameter) | 2.3–2.4 mm. | 2.9–3.1 mm. |
| Stem Diameter | 6–8 mm. | 8–14 mm. |

-continued

| | Chart A | |
|---|---|---|
| | White Butterfly | Magnum |
| Leaf Length (apex to base of longest lobe) | 11.6–15.6 cm. | 17–20.5 cm. |
| Leaf Width (at juncture of petiole) | 7–8.4 cm. | 10.4–11.8 cm. |
| Leaf Length (apex to juncture of petiole) | 6.8–9.2 cm. | 10.5–12.5 cm. |
| Length/Width Ratio | (1.6)1.8–1.9 | 1.5–1.8 |
| Leaf Thickness at Thinnest Part (between veins) | 0.14–0.24 mm. | 0.24–0.31 mm. |
| Petiole Diameter (at juncture of sheath) | 3.1–4.6 mm. | 4.7–5.2 mm. |

I claim:

1. A new and distinct variety of *Syngonium podophyllum* named Magnum, as illustrated and described, and particularly characterized by its large leaves, large diameter stem and petioles, with the petioles carrying the leaves very erect; and by its full appearance.

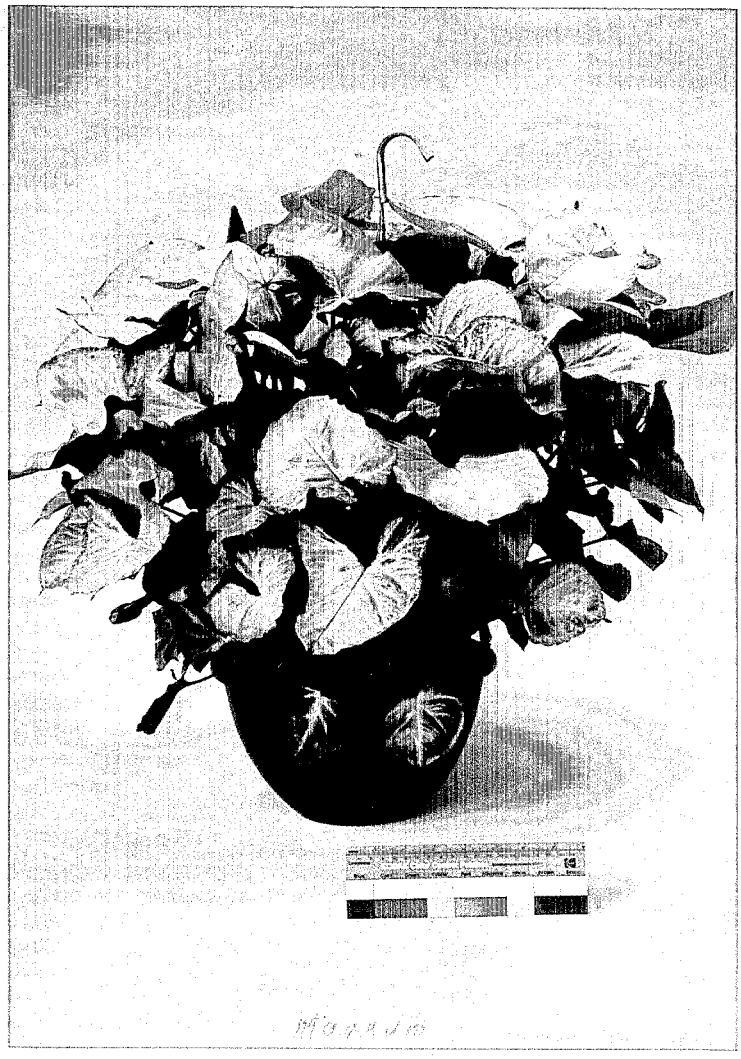
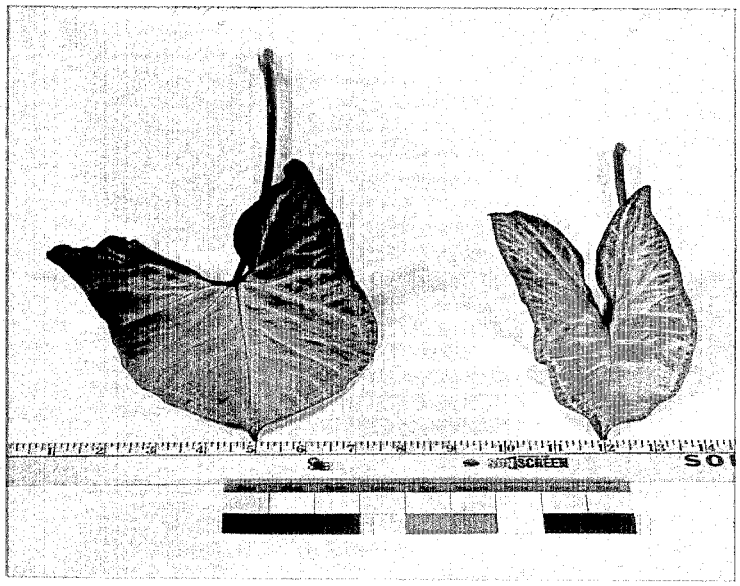

* * * * *